(12) United States Patent
Kelly et al.

(10) Patent No.: US 6,278,412 B1
(45) Date of Patent: Aug. 21, 2001

(54) METHOD AND MEANS FOR MOISTURE MEASUREMENT

(75) Inventors: Richard Kingswood Kelly, Toorak Gardens; Krzysztof Marian Kuchar, Glynde, both of (AU)

(73) Assignee: Vomax Pty Ltd. (AU)

( * ) Notice: Subject to any disclaimer, the term of this patent is extended or adjusted under 35 U.S.C. 154(b) by 0 days.

(21) Appl. No.: 09/262,152

(22) Filed: Mar. 3, 1999

(30) Foreign Application Priority Data

Mar. 3, 1998 (AU) .................................................. PP 2114

(51) Int. Cl.⁷ .................................................. G01N 23/00
(52) U.S. Cl. ............................................ 343/786; 324/640
(58) Field of Search ..................................... 343/878, 703, 343/786; 324/637, 639, 501, 640, 644, 376, 840

(56) References Cited

U.S. PATENT DOCUMENTS 2,659,860  11/1953  Breazeale ................................ 324/49
5,006,785 *  4/1991  Revus et al. .......................... 324/639
5,621,330     4/1997  Greenwald et al. .................. 324/640
5,631,661 *  5/1997  Sanchez ................................ 343/703
5,698,978 * 12/1997  Darling et al. ....................... 324/238
6,025,724 *  2/2000  Moshe et al. ........................ 324/640

OTHER PUBLICATIONS

Microwave Aquametry Andrzej Kraszewski 1993 IEEE Press, pp. 3–34, pp. 313–327.

* cited by examiner

Primary Examiner—Tan Ho
Assistant Examiner—James Clinger
(74) Attorney, Agent, or Firm—Akerman Senterfitt

(57) ABSTRACT

A microwave transmission antenna arrangement for transmission of microwave signals from a position located in the adjacent vicinity of a bale transfer apparatus for transporting bales past the antenna for assessment of bale characteristics such as moisture in cotton including an antenna supported by a forgiving support by being relatively movable in position if a bale intercepts the antenna. The antenna is supported so as to be restored to a transmission and/or receiving position subsequent to any dislodgment as a result of any interception of a bale.

14 Claims, 8 Drawing Sheets

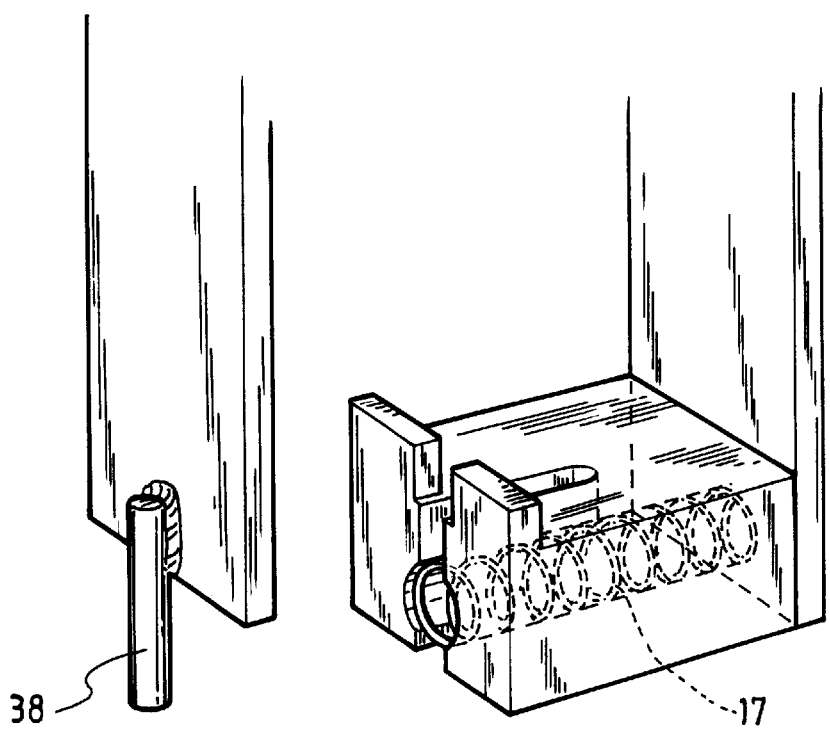
FIG 10
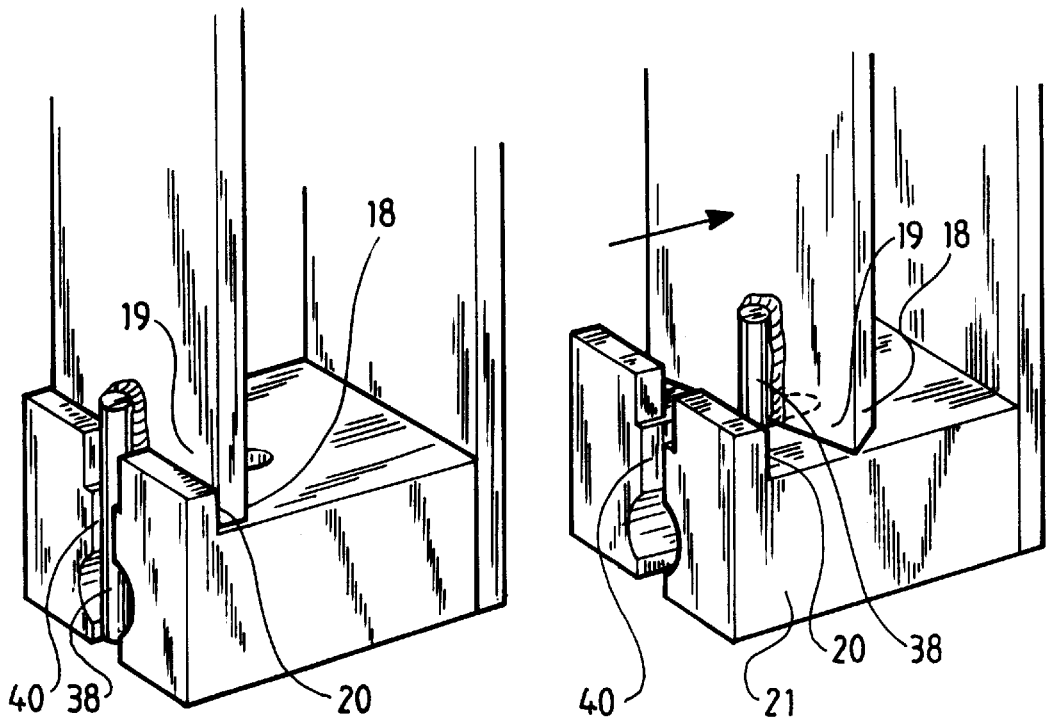
FIG 11  FIG 12

METHOD AND MEANS FOR MOISTURE MEASUREMENT

This invention relates to a method and means for measuring characteristics of a materials by using microwaves transmitted through the materials.

Use of such a technique in general terms has been well known for a number of years, and as an example, U.S. Pat. No. 2,659,860 describes the use of attenuation of microwaves as a useful technique for the detection of an extent of moisture in material of known density.

There have however been a number of technical and cost difficulties with this technique which has prevented this technique from revolutionising the industry and some of these have been appropriately described in U.S. Pat. No. 5,621,330.

A major application for this technique is the measurement of moisture in packed materials and in particular cotton so that a total quantity of moisture can be assessed.

Cotton, subsequent to processing which includes removal of seeds and other unwanted materials, is packed into bales and it is the moisture content of the cotton in each bale that is of some importance. This can be in the form typically of processed cotton bales or raw(seed) cotton in incoming module form.

The features of this invention have particular application to cotton and to cotton bales but are not specifically limited in their broadest application to simply cotton, and can in a broadest sense apply to any organic material.

A characteristic of a cotton bale is that it is made by tramping individual charges of cotton into a holding means after which they are pressed and then bound by straps or wires and held thereafter in a bale shape.

Each charge of cotton however is easily separable from adjacent charges and in practice, each charge forms a layer in the bale so that the bale is then made up from a number of these layers which are easily separable if the bale is eventually opened out or broken down.

Further however, each charge of cotton forming a layer tends to have more consistent characteristics within the charge or layer than might occur across the layer or in adjacent charges forming other layers.

Using a microwave transmission and reception system then with respect to such bales has a number of significant problems unless the bale when being measured is aligned so that the microwave energy from transmitter to receiver whether this is so as to pass fully through the bale or to be passed through and back again through the bale, passes substantially in the alignment direction of the individual layers. In other words, most of the microwave energy then would be expected to pass through a single individual layer and it is therefore the measurement of the characteristics of that layer which will be measured.

It has been previously considered not practicable to use what might be termed an orthogonal measurement technique for reasons some of which will now be explained.

A first of these reasons is that when the bale is constructed, and recalling that the all up mass of a bale can be very large indeed, the so-called height of the bale is not accurately defined.

It is understandable as to why this would be the case, but this does not help the situation when the bale is to be laid on a conveyer belt and a transmitter and receiver for microwave energy is to be located as close as feasible to the sides of the bale. This is done In order to minimise stray reflections or losses occasioned by passing microwave energy through the air a variable distance from the side of the bale.

If the bale therefore is not entirely accurately placed on a conveyer belt or its height (it is height when it is manufactured but it is laid over when it is on a conveyer belt so that the height is in fact a reference to the effective width for purposes of measurement of characteristics) can be such that the bale itself can impinge on a part of the microwave transmission or receiving equipment and the moment that this occurs then this destroys the accuracy of the system and substantial and urgent repairs with existing equipment may be necessary.

Further, while it has been considered that if it was possible it would provide a more uniform measurement if a measurement could be taken orthogonally, nonetheless, there appears to be internal reflections caused by boundaries between the layers that interferes with the microwave that has been previously attempted to be transmitted through these making any results difficult to interpret or not sufficiently accurate for commercial purposes.

To the applicant's knowledge therefore measurement of characteristics of a cotton bale using microwave attenuation or change has always occurred by passing the microwave energy substantially in the direction along layers within a bale.

We have found that we can now effectively measure characteristics of a cotton bale by directing microwave energy orthogonally to the previously accepted direction.

In other words, we can now effect a commercial system for assessment of characteristics of a cotton bale where the predominant direction of the microwave energy is from layer to layer so that the microwave energy passes through all or substantially all of the layers during a measurement.

There is one significant advantage in doing this which is that such a reading will be affected by the degree of moisture in each of the layers so that the one reading becomes implicitly a reading effected by the total measure of moisture in the bale or at least a reasonable sample of the moisture in each layer.

How have we overcome the implicit problems however.

In accordance with this invention then this can be said to reside in a microwave transmission antenna arrangement for transmission of microwave signals from a position located in the adjacent vicinity of a bale transfer apparatus for transporting bales past the antenna for assessment purposes characterized in that the antenna is supported so as to be a forgiving support by being relatively movable with respect to a support base.

In preference, the antenna is supported with means to restore to a transmission and/or receiving position the position of the antenna subsequent to any relative dislodgment movement.

Further, there are means to detect such displacement.

In a production facility however, it is not good enough simply to know that the equipment has been displaced but it is also a preferred feature that the antenna shall be supported so that subsequent to any dislodgment, it will be restored to an accurate transmission and/or receiving position.

In a preferred arrangement, there is a spring loaded mounting holding an antenna in position against matching faces.

A next problem however is that because the bale when it is being positioned with its indeterminate height now determining the width, it becomes preferable even with forgiving mounts to allow for a larger air gap between the transmission and receiving antenna and the side of the bale.

This introduces the problem that if the antenna is in the form of a horn in which the larger end of the horn then is adjacent an expected side of the bale, then the horn itself becomes accessible to incoming microwave signals which can be coming from a diverse number of directions.

In preference, there is then provided microwave absorption means positioned in the vicinity of the entry location of signals into the receiving antenna.

In preference, such microwave absorbing surface surrounds and is positioned to be more likely to absorb microwaves which are being directed other than directly into the antenna.

In preference, the antenna is in the shape of a horn and there is microwave absorption material located and of a shape such as a collar surrounding an end of the horn the position of the internal surfaces of the collar being such as to define a passageway of approximately rectangular dimensions matching an outer rectangular dimension of the horn and having parallel sides aligned so as to be also parallel to a main access of the horn.

In preference, the microwave absorption surfaces exhibit absorption at the appropriate frequency of at least 5 dB.

In preference, in accordance with a further feature, the frequency has been found to be a significant factor in getting the method of the invention to be effective and matching this with allowable frequency ranges by reason of external regulators, a frequency within the range from 2.40 to 2.45 gigahertz has been found to be preferred.

A further preferred feature has been to provide a microwave absorber shield behind each of the transmitters or receivers so as to additionally reduce stray transmissions or reflections which will also interfere with accurate readings.

It is to be understood that the invention is directed to a method of measuring characteristics of a bale which has advantages.

The equipment itself however can be used for measurement of characteristics of a bale located in a more conventional orientation which is to say with the alignment such that the microwave direction will extend substantially along a respective layer.

Use of microwave energy for the general purpose of measurement of characteristics of a material is known. It has been found in connection with this invention that one method of assessment that has been found to be of particular use uses both measurement of an extent of attentuation of a signal through a bale and as well as velocity of a signal through the material. Velocity change is able to be obtained by measuring an extent of change of phase through a range of different frequencies. Attenuation of a signal is effected by both bulk density of the material eg cotton as well as moisture content. Velocity change is also affected by bulk density and moisture content but to a differential extent between these as compared with an effect on attenuation of the signal. This then provides a basis by which an assessment of moisture can be calculated.

In another method either attentuation alone or velocity change alone is used and the total weight of the bale is then used to make an assessment of the moisture content of the bale of material.

In this invention it is assumed that any one of the above methods can be used especially but not exclusively where the direction of measuring microwave signals is chosen to be orthogonal to a layer alignment within a bale of the material.

The invention can be directed to means and to a method to achieve the object of the invention.

For a better understanding of this invention it will now be described in relation to a preferred embodiment which shall be described with the assistance of drawings wherein:

FIG. 10 is an exploded view of a detail of the assembly;

FIG. 11 a view of the assembly detail in a connected and supporting position; and FIG. 12 a view of the assembly detail in a dislodged position.

Figure 1:
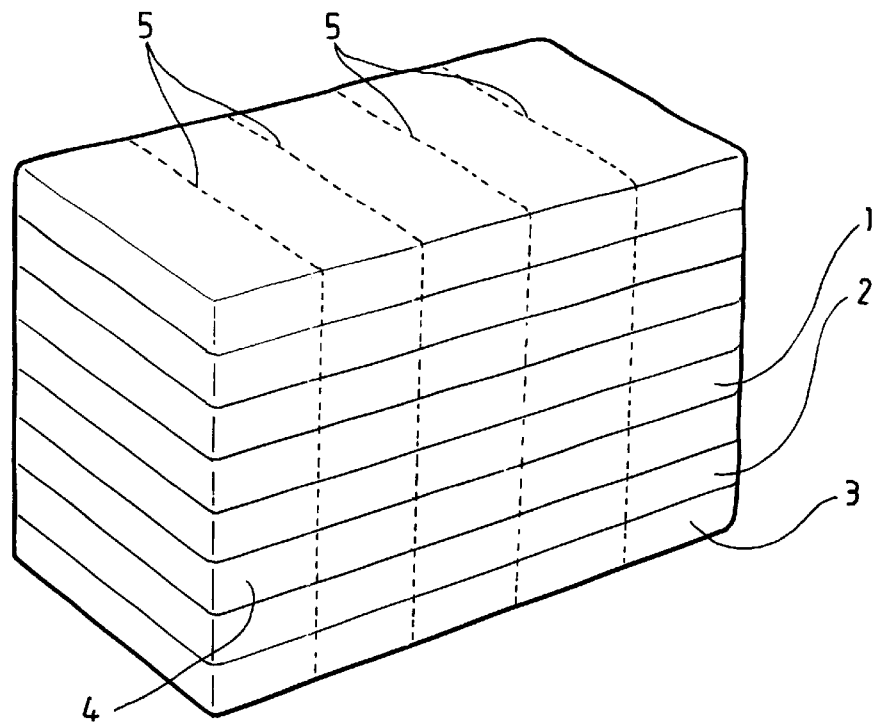
FIG. 1 is a perspective view of a bale of the type to be measured where the orientation is so that the respective layers extend in an approximately horizontal position which is the current position as formed.
Figure 2:
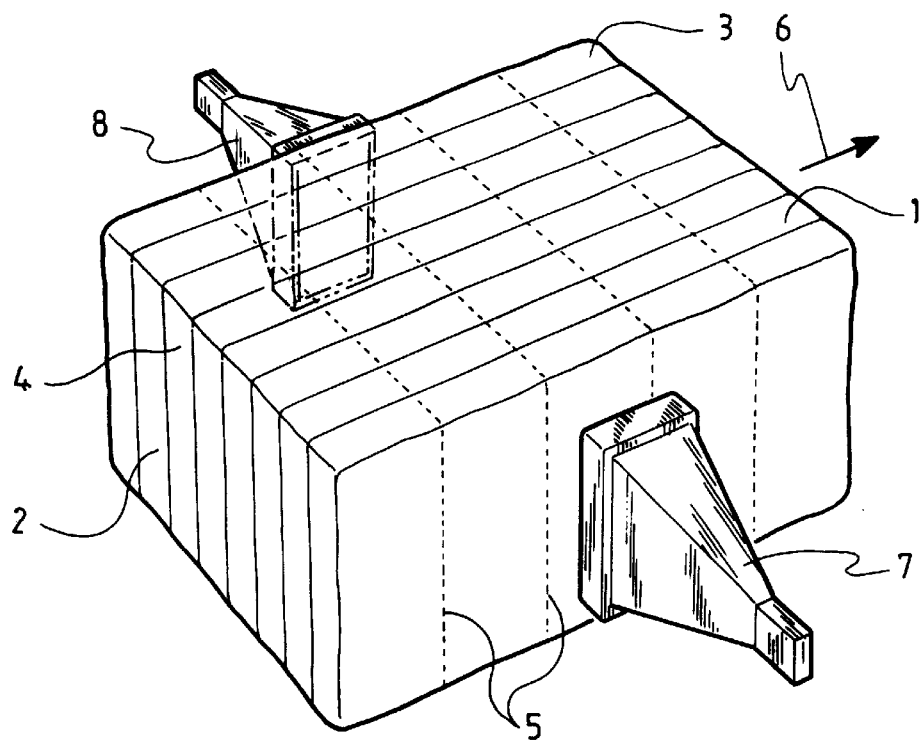
FIG. 2 is a perspective view of the bale as in FIG. 1 now laid on its side and having respective horns on each side in a measuring position showing the orientation that is to be used in accord with this embodiment.
Figure 3:
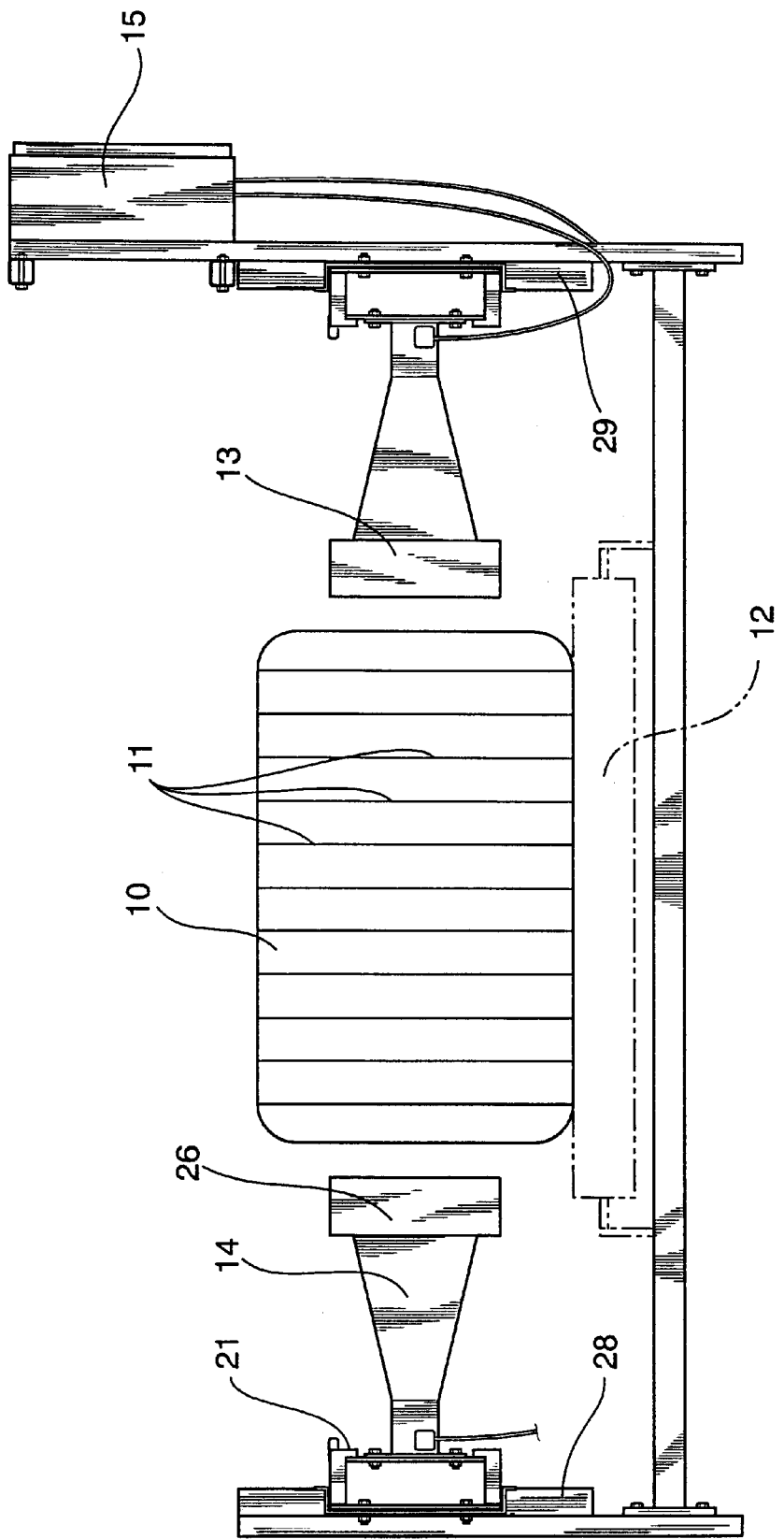
FIG. 3 is an end view of an assembly in accordance with the embodiment incorporating a bale and appropriately positioned horns on each side.
Figure 4:
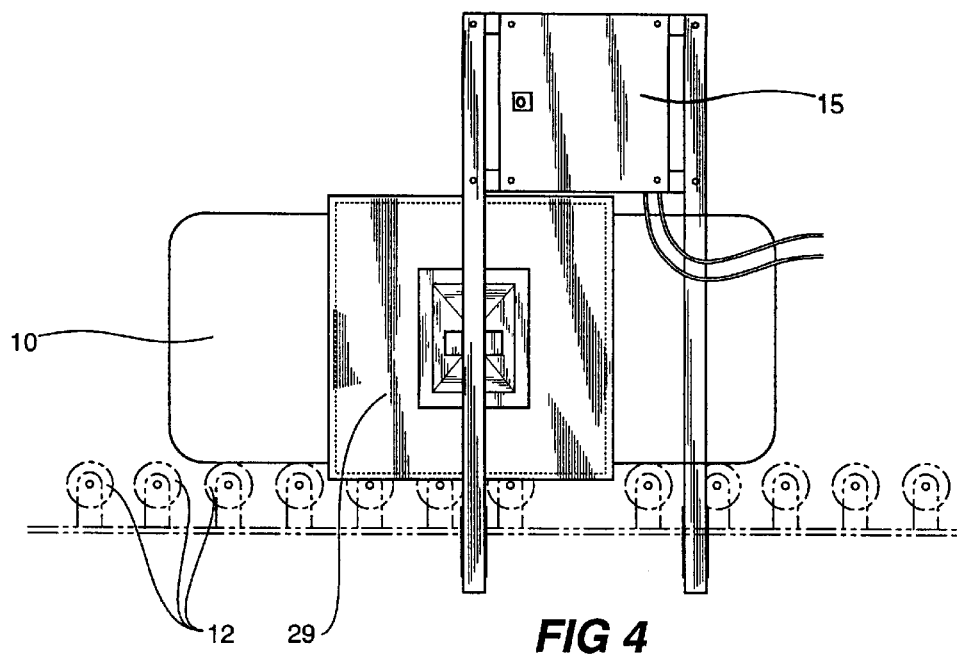
FIG. 4 is a side view of the assembly as shown in FIG. 3.
Figure 5:
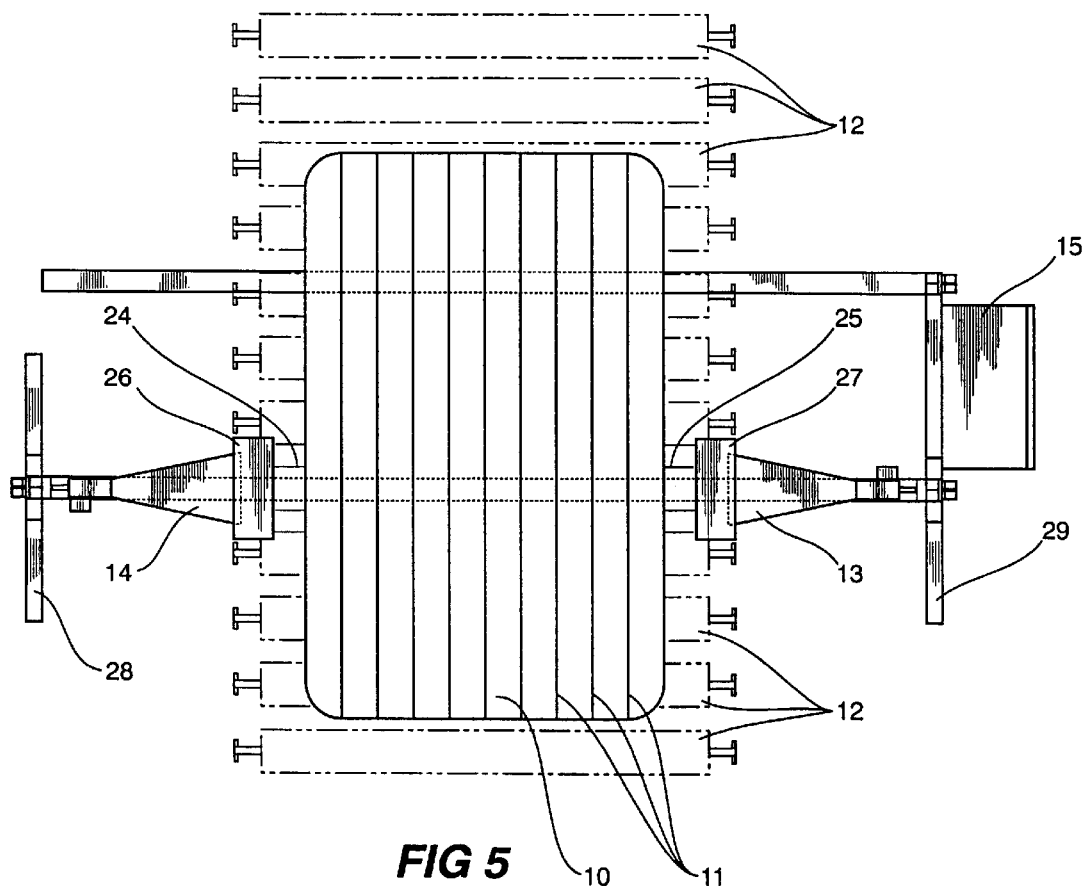
FIG. 5 is a plan view of the assembly as shown in FIGS. 3 and 4.
Figure 6:
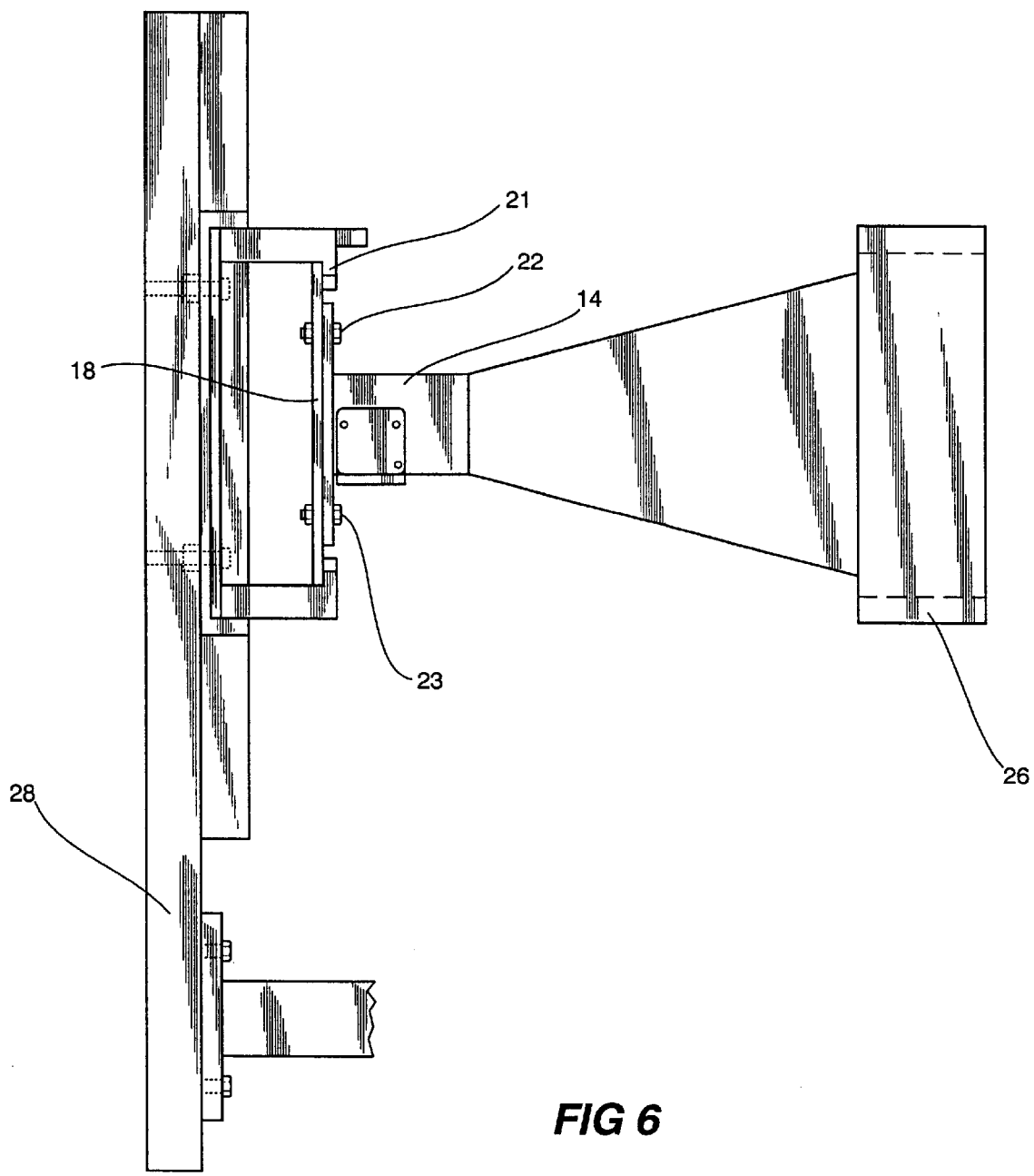
FIG. 6 is an enlarged view of a portion of the assembly shown in FIGS. 3, 4 and 5.

Now describing the embodiment, we refer firstly to FIG. 1 in which the bale 1, is comprised of compressed cotton and is constructed in accordance with a conventional technique so that during ginning, layers of cotton are pressed into a bale shape so that respective layers are aligned one on lop of the other.

These layers are shown typically at 2, 3, 4 and so on.

Each layer comprises a full layer across the full width of the bale 1 and as can be expected in the manner of natural materials, will provide an inherent boundary surface between the respective layers that these can be discerned and can be subsequently established by subsequently separating the bale into separate layers so that they could be separately distinguished in this way.

The layers are collectively held together by surrounding bands 5 of wire which are tightly wound around the cotton layers;

In this way however the actual height is not accurately foreseen although it is known generally to be within giver limits (+ or −5 cms might be typical).

The bale shown in FIG. 1 is as the bale is conventionally formed, and for the purposes of this invention, it will be laid over so that the former height now becomes the width and the bale will then be moved in the direction of arrow 6 so that with transmission or receiving horns such as 7 and 8 the direction of the microwave energy generated from these will necessarily pass orthogonally through the bale in respect of the orientation of each of the respective layers.

This is in contradiction to what has been always previously the case where the microwave energy is directed from one end of the bale through the same layer or adjacent layers to an alternate end.

Now referring to FIGS. 3, 4, 5, 6 and 8, there is shown in this case then a bale which will now be referred to as 10 in which there are a plurality of layers shown typically at 11 with the alignment of these layers being in the direction of forward motion of the bale which is being supported on a conveyer shown typically by the rollers at 12.

There are transmitting and receiving horns shown now at 13 and 14 and associated electronic controls in a controlled module at 15.

The two horns 13 and 14 acting as either a transmitter or a receiver in connection with microwave energy selected in this embodiment to be within the range of from 2.40 to 2.45 gigahertz, are each supported so that in their normal position they are accurately aligned so as to accurately coincide with the respective transmissions or receiving microwaves of the other antenna.

Figure 8:
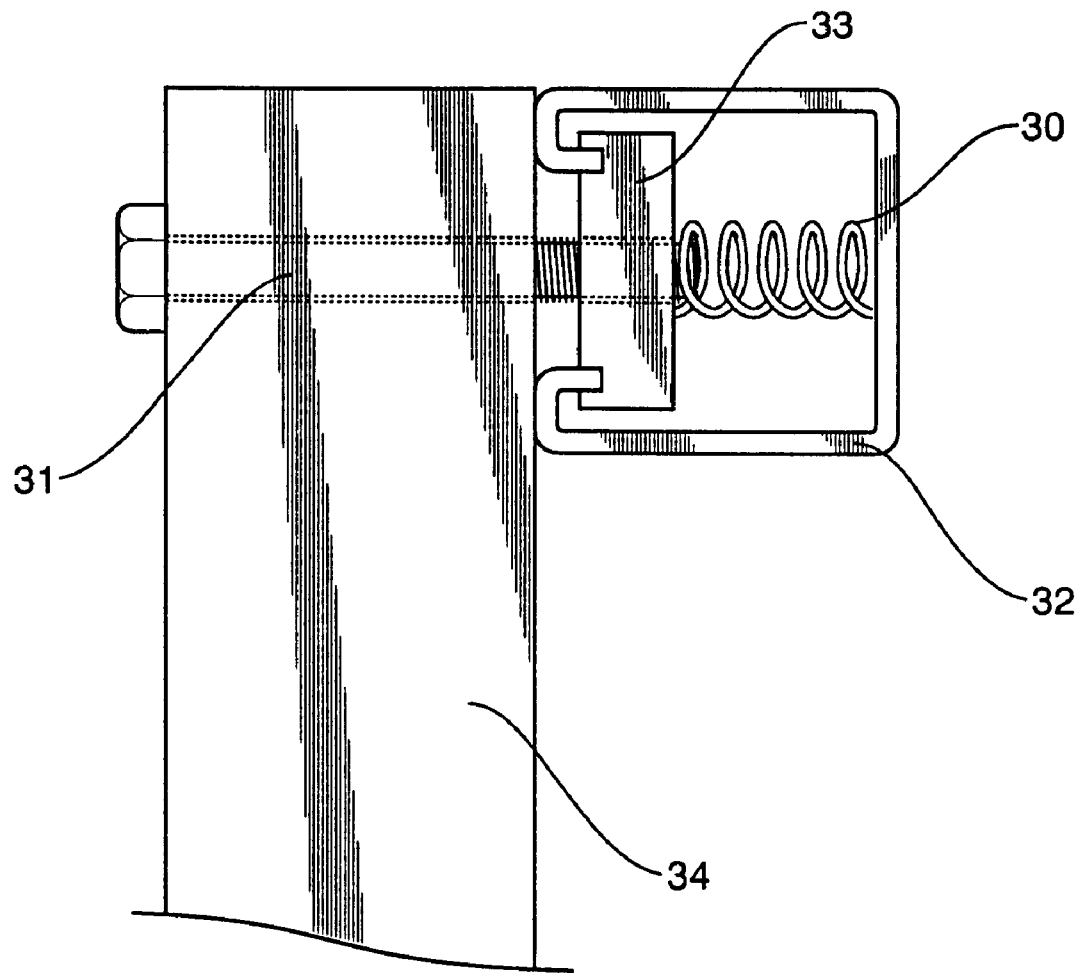
FIG. 8 is an alternate arrangement for supporting in a forgiving way the respective horns in accordance with the embodiment as shown in FIGS. 3 through 6.

Each horn however is supported by a forgiving support assembly such that it can be diverted momentarily from an accurate alignment but by reason of a spring return shown for instance at FIG. 8 at 16 in the one case and 17 in the other, a flat plate 18 has a forward face at 19 which is held against a flat face 20 of a bracket 21. A tongue at 37 and 38 is located to fit into a slot 39 in the one case and 40 in the other to ensure alignment in a forward to rearward direction as well as orientation.

The horn 14 is supported through bolts 22 and 23.

In existence but not shown, there is a micro switch which is operated upon even a very small displacement relative position of the two members 18 and 21 which switch then signals to an operator or to the software program that any reading should not then be taken or if it is, to be disregarded.

By reason of spring loading, as soon as the force dislocating the position of a horn is past is dislocating position, the horn will revert to an accurately aligned position and conventional readings will then continue to take place.

In order to inhibit stray reflections because of the larger tolerance now necessary between an end of the horn and an edge of the bale for instance as typically shown at 24 and 25, there is the feature of providing a surrounding collar or blinker 26.

Figure 9:
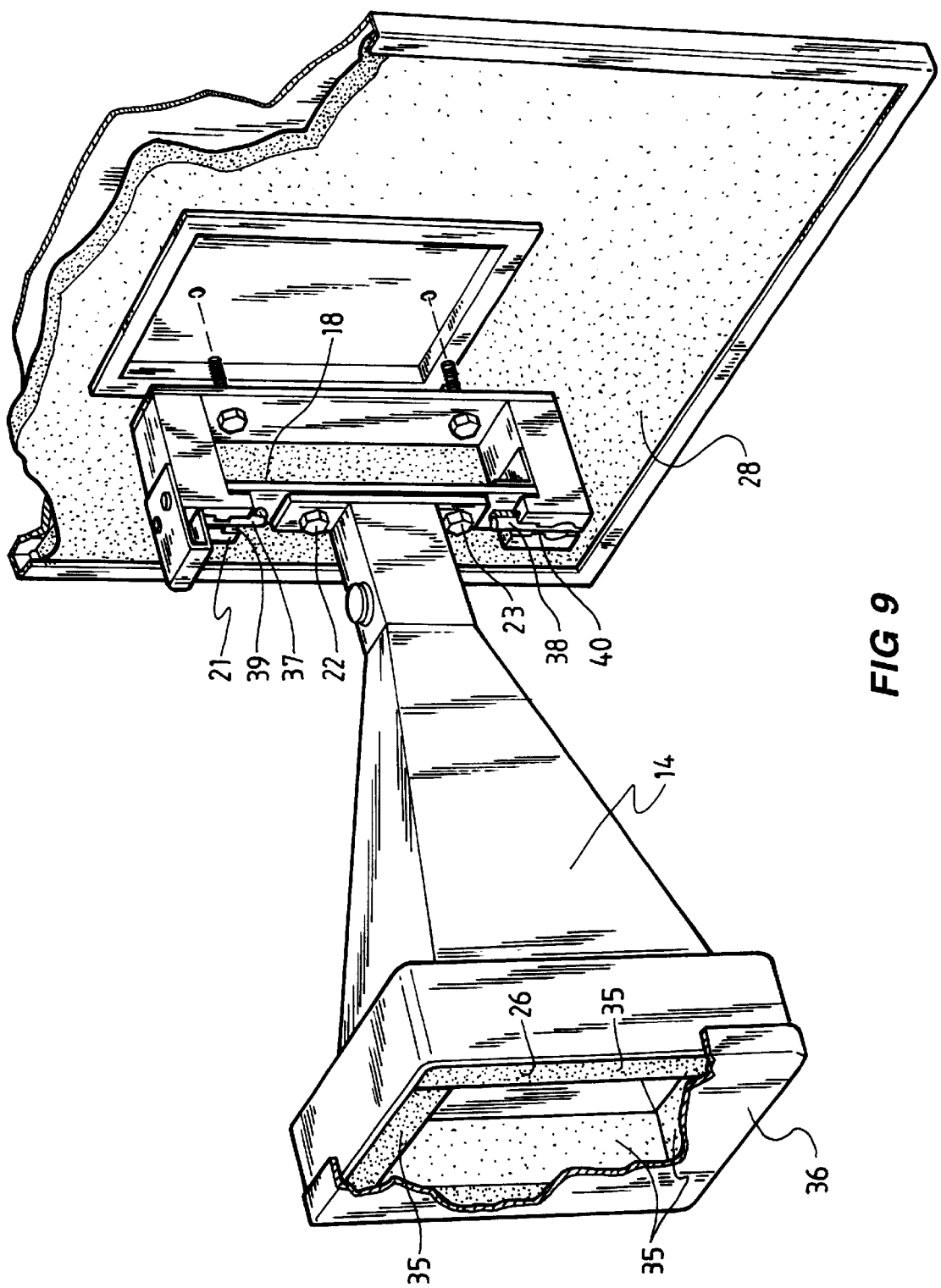
FIG. 9 is a perspective and exploded view with part cutaway of the assembly as in the previous FIGS. 3, 4, 5, 6, and 8.

This is comprised of microwave absorbing foam slabs 35 shown in FIG. 9 of a type that is conventionally commercially available and has an absorption in the 2.40 gigahertz range of 20 dB. A cover 36 which is selected to be of material transparent to the microwaves is positioned across the aperture. This is positioned so that an inner surface is parallel to an alignment of microwave transmission so that any stray transmission which might be coming from a quite acute angle, will now have a greater probability of hitting the absorbing material within the front collar and therefore not be so likely to cause misleading or confusing readings.

Such an arrangement is positioned in both horns in this case.

A further advantageous arrangement includes a broad shield of microwave absorbing foam behind each of the horns these being shown respectively at 28 in the one case and 29 in the other.

While reference has been made to mounting both antennas on forgiving supports, it can be envisaged that there be provided simply one of the antennas being provided on a forgiving support where the other antenna is protected by a diversion member so that all of the variation in width of a bale will be represented by movement or change in position on one side only.

This is not the preferred system but is another example of an embodiment.

Figure 7:
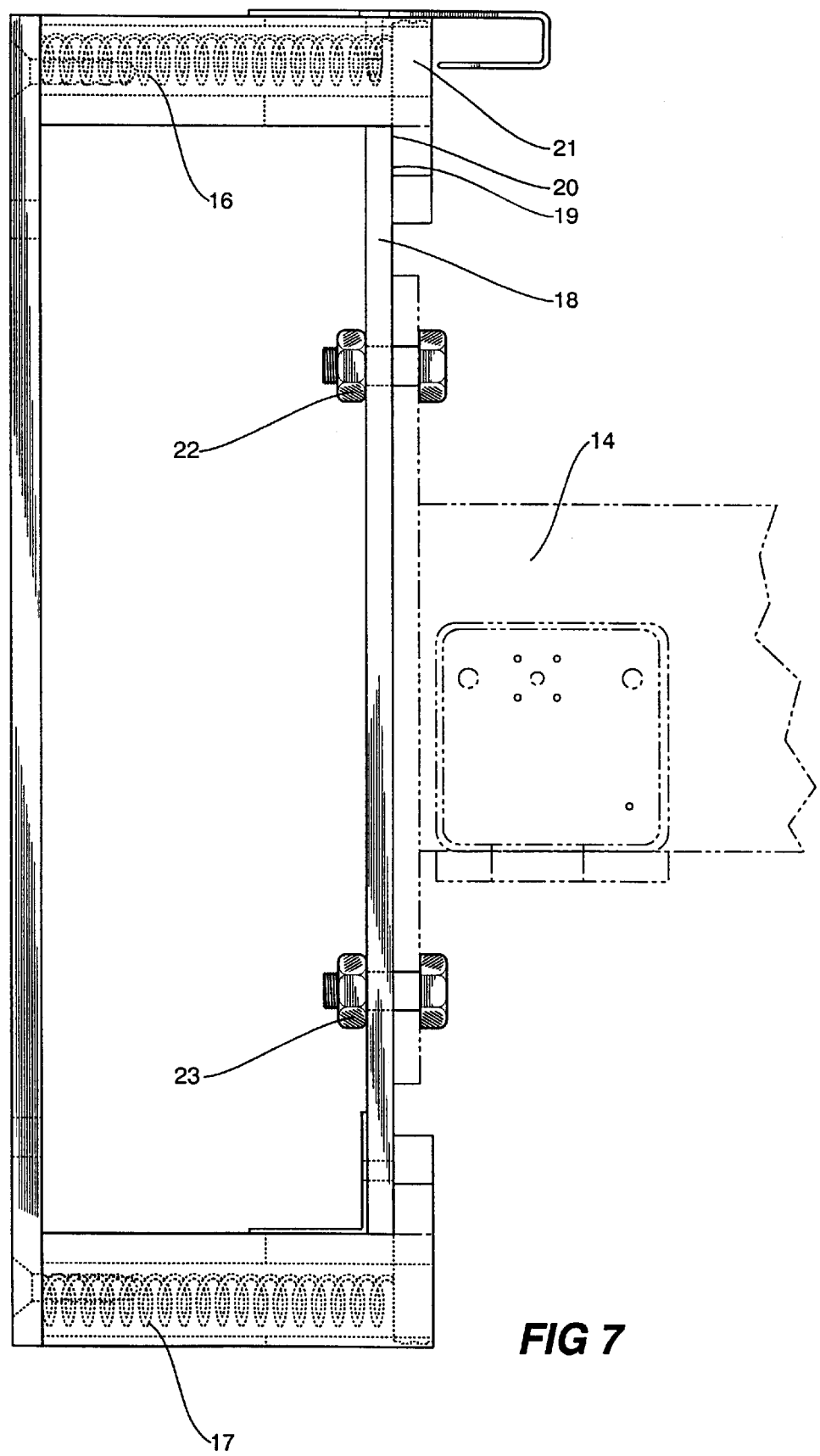
FIG. 7 is a detail of one example of a forgiving support arrangement for the horn.

Likewise, in FIG. 7 there is shown an alternative spring loaded support system in which a spring 30 is aligned by bolt 31 and contained within channel 32 so as to keep in alignment member 33.

Beam 34 is thereby supported relative to channel 32 so that the two can be dislodged one with respect to the other but the spring will cause a returning force and relocate with accurate alignment subsequent to the dislodgment force.

This is simply to show that there is an alternate system and there can be others.

In measurements conducted so far, it has been found that the potential width variation of bales being measured in accordance with this invention sun be as much as + or −5 cm and the tolerances are appropriately selected.

As will now be seen, it becomes effective in a commercial sense to transmit a microwave signal for measurement purposes through the layers of the cotton layers in a bale which is in the orthogonal position to that which has been conventionally used.

This allows a moisture reading to be taken that is representative of the bale as a whole rather than as a particular layer of cotton in the bale. This is also advantageous, as there are no set number of layers in a cotton bale—the number of layers may range typically between 11 and 18.

Accordingly, in a system which requires to take sampling of one layer in particular, not only does it require to then 'guess' the moisture of other layers in the bale, but it also needs to allow for the fact that the signal may be transmitting between two layers rather than through a single layer.

According to another feature, in accordance with this embodiment, there can be provided that measurements can be taken on a bi directional basis. That is, the signal is switched from respective horns to become transmitter or receiver thus allowing for corrections to be made for any directional bias that might be due to lack of homogeneity or symmetry in the operating systems environment. In trials, it has been shown that on average these have had a standard deviation of two thirds of that obtained for a uni-directional system. That is by having alternating receive and transmit rolled through a sequence of readings in connection with the same bale, there is provided an approximately 30% improvement in accuracy.

A further feature of the embodiment is that the system is capable of measuring the VSWR at the transmitting horn and thus determine if the bale is not properly positioned between the horns. The value obtained can then be applied to a model equation in order to correct the positioning of the bale as well as serve as a warning signal that the space between either of the horns might be becoming too small or too large.

What we claim is:

1. A microwave transmission antenna arrangement for transmission of microwave signals from a position located in the adjacent vicinity of a bale transfer apparatus for transporting bales past the antenna for assessment of bale characteristics, comprising a transmitting antenna and a receiving antenna, at least one of which is supported by a support having means to restore the position of the antenna to a transmitting or receiving position subsequent to any dislodgement as a result of being engaged by a bale, wherein the support is a spring loaded mounting holding the antenna in position by reason of alignment of a first face with respect to a second face, the first face being provided on a plate and the second face being provided on a bracket.

2. A microwave transmission antenna arrangement as in claim 1 further comprising microwave absorption surfaces positioned in the vicinity of an entry location of signals into the receiving antenna.

3. A microwave transmission antenna arrangement as in claim 2, wherein the microwave absorbing surfaces surround the antenna and are positioned to be more likely to absorb microwaves which are being directed in a direction other than those passing directly into the antenna.

4. A microwave transmission antenna arrangement as in claim 2, wherein the microwave absorption surfaces comprise microwave absorbing foam slabs having an effective and substantial absorption of microwave in the 2.40 gigahertz range of at least 20 dB.

5. A microwave transmission antenna arrangement as in claim 1, wherein each of the antennas is in the shape of a horn.

6. A microwave transmission antenna arrangement as in claim 5, wherein there is microwave absorption material providing a microwave absorption surface being a collar surrounding an end of the horn shape of each antenna, the position of the internal surfaces of the collar defining a passageway of approximately rectangular dimensions matching an outer rectangular dimension of the horn and having parallel sides aligned so as to be also parallel to sides of the horn.

7. A microwave transmission antenna arrangement as in claim 5, wherein there is microwave absorption material providing a microwave absorption surface being a collar surrounding an end of the horn shape of each antenna, the position of the internal surfaces of the collar defining a passageway of approximately rectangular dimensions matching an outer rectangular dimension of the horn and having parallel sides aligned so as to be also parallel to sides of the horn, wherein the microwave absorption surfaces exhibit substantial absorption at a frequency of at least 5 dB.

8. A microwave transmission antenna arrangement as in claim 1, wherein each of the antennas is adapted to be used at a frequency within the range from 2.40 to 2.45 gigahertz.

9. A microwave transmission antenna arrangement as in claim 1, wherein there is a microwave absorber shield behind each of the transmitters or receivers adapted to reduce stray transmissions or reflections.

10. A microwave transmission antenna arrangement as in claim 1 wherein each antenna is in the form of a horn and such that there are two antennas of this shape each of which respectively act as either a transmitter or a receiver in connection with microwave energy selected to be within the range of from 2.40 to 2.45 gigahertz, and are each supported so that in their normal position they are aligned so as to coincide with the respective transmissions or receiving microwaves of the other antenna.

11. A microwave transmission antenna arrangement as in claim 1, wherein the spring loaded mounting comprises a spring return, a flat plate having a forward face engaging against a matching face of a bracket and a tongue located to fit into a slot whereby to ensure appropriate alignment of the antenna in a forward to rearward direction as well as appropriate orientation for measuring using microwave purposes.

12. A microwave transmission antenna arrangement as in claim 1 further comprising a position detector which is arranged to be effected upon a displacement of one or more of the two antennas whereby an electrical signal warning of such displacement can be effected.

13. A microwave transmission antenna arrangement as in claim 1, wherein one only of the antennas is provided with said spring loaded mounting.

14. A microwave transmission antenna arrangement for transmission of microwave signals from a position located in the adjacent vicinity of a bale transfer apparatus for transporting bales past the antenna for assessment of bale characteristics, comprising a transmitting antenna and a receiving antenna, at least one of which is supported by a support having means to restore the position of the antenna to a transmitting or receiving position subsequent to any dislodgement as a result of being engaged by a bale, wherein the support is a spring loaded support system in which a spring is aligned by a bolt and contained within a channel so as to keep alignment thereby.

* * * * *